United States Patent [19]

Cantin et al.

[11] Patent Number: 5,110,802
[45] Date of Patent: May 5, 1992

[54] OLIGONUCLEOTIDE PHOSPHONATES AND METHOD OF INHIBITING A HUMAN IMMUNODEFICIENCY VIRUS IN VITRO UTILIZING SAID OLIGONUCLEOTIDE PHOSPHONATES

[75] Inventors: Edouard M. Cantin, Los Angeles; John A. Zaia, Arcadia; R. Bruce Wallace, South Pasadena; John J. Rossi, Glendora, all of Calif.

[73] Assignee: City of Hope, Duarte, Calif.

[21] Appl. No.: 73,189

[22] Filed: Jul. 14, 1987

[51] Int. Cl.$^5$ .............................. A61K 31/70
[52] U.S. Cl. ........................ 514/44; 536/27; 536/28; 536/29; 435/6
[58] Field of Search .............. 536/27, 28, 29; 514/44

[56] References Cited

U.S. PATENT DOCUMENTS 4,469,863  9/1984  Ts'O et al. ........................ 536/27

FOREIGN PATENT DOCUMENTS 8702989  6/1985  World Int. Prop. O. .

OTHER PUBLICATIONS

Guyadet et al., Nature, vol. 326, pp. 662–669, 1987.
Arya et al., P.N.A.S. USA, vol. 83, pp. 2209–2213, 1986.
Alizon et al., Cell, vol. 46, pp. 63–74, 1986.
Barone et al., J. of Immunology, vol. 137(2), pp. 669–673, 1986.
Sandstrom et al., Drugs, vol. 34, pp. 372–390 (1987).
Mitsuya et al., "Protection of T Cells against Infectivity and Cytopathic Effect of HTLV-III In Vitro Retroviruses in Human Lymphoma/Leukemia", Miwa et al. eds., VNU Science Press, Utrecht, 1985, pp. 277–288.
Altmann, "AIDS Epidemic Puts an Unusual Microbe Under Scrutiny", The N.Y. Times, New York, Jun. 26, 1990, p. C3.
Zamecnik et al., Proc. Nat. Acad. Sci. USA, vol. 83, pp. 4143–4146, 1986.

*Primary Examiner*—Johnnie R. Brown
*Assistant Examiner*—L. Eric Crane
*Attorney, Agent, or Firm*—Edward S. Irons

[57] ABSTRACT

A method of inhibiting human immunodeficiency virus (HIV) comprising administering a therapeutically effective amount of an antiviral agent to attack the first splice acceptor site of the tat III gene of HIV.

5 Claims, 2 Drawing Sheets

A B C D E F

OLIGONUCLEOTIDE PHOSPHONATES AND METHOD OF INHIBITING A HUMAN IMMUNODEFICIENCY VIRUS IN VITRO UTILIZING SAID OLIGONUCLEOTIDE PHOSPHONATES

This invention was made with government support under Grant No. U01 CA34991 awarded by the National Institutes of Health. The government has certain rights in the invention.

BACKGROUND OF THE INVENTION

This invention relates to a method of treating Acquired Immune Deficiency Syndrome (AIDS) in humans using antisense oligodeoxynucleoside methylphosphonates.

It is known that organisms have exploited a wide variety of mechanisms for regulating gene expression. Green, P. J., et al., *Ann. Rev. Biochem* 55: 569-597 (1986) reported that naturally occurring regulatory genes direct the synthesis of RNA which can directly control gene expression. The term "antisense RNA" has been coined to describe this regulatory RNA. Antisense RNA is complementary to and therefore can form base pairs with a specific mRNA. The naturally occurring antisense RNA discovered to date has been in bacterial systems. The discovery of this natural phenomenon has led to the exploitation of antisense RNA and DNA to inhibit the expression of a wide variety of gene products by interference with activities such as pre-mRNA splicing, mRNA transport to the cytoplasm, and translation of the mRNA itself. Of particular interest is the use of nucleic acid sequences complementary to viral gene targets in the human immunodeficiency virus (HIV) or human T-lymphotropic virus (HTLV-III/LAV), the etiological agents of AIDS.[1]

[1] A., Hollander, H. and Stobo, J. *Ann. Rev. Med.* 36. 545-562 (1985); Wong-Staal, F. and Gallo, R. C., *Nature* 317, 395-403 (1985); Rabson, A. B. and Martin, M. A. *Cell* 40, 477-480 (1985).

It is known that HIV, a retrovirus, infects T-lymphocytes by recognizing the T4 antigen,[2] and that brain cells and macrophages are also targets for the viral infection.[3] The viral sequence of HIV has been determined to include genes for the structural proteins of the virus which are designated gag, pol, and env. These genes are bounded by the long terminal repeats (LTRs). There are also accessory genes in the HIV genome which are involved in controlling virus replication, including at least three genes which code for trans-activator (tat) regulatory protein.[4]

[2] Dalgleish, A. B. et al., *Nature* 312, 277-284 (1985); Maddon, P. J., et al., *Cell* 47, 333-348 (1986); McDougal, J. S., et al., *J. Immunol.* 135, 3151-3162 (1985).
[3] Epstein, L. G., et al., *AIDS Res.* 1, 447-454 (1985); Ho, D. D., et al., *N. Eng. J. Med/* 313, 1498-1504 (1985); Koenig, S., et al., *Science* 233, 1089-1093 (1986); Levy, J. A., et al., Lancet 11, 586-588 (1085); Sharer, L. R., et al., *Human Path.* 17, 271-284 (1986); Shaw, G. M., et al., *Science* 227, 177-182 (1985).
[4] Sodroski, J., et al., *Nature* 321, 412-417 (1986); Rosen, C. A., et al., *Nature* 319, 555-559 (1986); Fischinger, P. J. and Bolognesi, D. P. in *AIDS* (ed. DeVita, Jr., V. T., Helman, S. and Rosenberg, S. A.) 55-58 (Lippincott Co., Philadelphia, Pa., 1985).

Oligodeoxyribonucleoside methylphosphonates (OMPs) are nucleic acid analogs in which a 3'-5' methylphosphonate linkage replaces the phosphodiester linkage found in naturally occurring nucleic acids. OMPs maintain the selectivity of complementary pairing exhibited by standard oligodeoxyribonucleotides and can be used as antisense agents. Miller, P. S., et al., *Biochimie* 67: 769-776 (1985) have shown that oligonucleoside methylphosphonates complementary to various regions of the rabbit globin mRNA inhibit translation of the RNA in a reticulocyte cell-free system. Herpes simplex type I virus has also been selectively inhibited using an antisense OMP targeted to its regulatory immediate early gene resulting in 99% reduction in infectious virus and a 75% reduction in viral DNA synthesis. Smith, C. C., et al., *Biochemistry* 83: 2787-2791 (1986).

SUMMARY OF THE INVENTION

In general, the invention features a method of inhibiting human immunodeficiency virus comprising administering a therapeutically effective amount of an antiviral agent to attack the first splice acceptor site of the tat III gene of HIV which site has the sequence 5' . . . AGAAUUGG . . . 3'.

In preferred embodiments, the antiviral agent is an oligodeoxyribonucleoside methylphosphonate complementary to the first splice acceptor site of the tat III gene having the sequence 3 ∝ TCTTAACC 5'.

Other advantages and features of the invention will be apparent from the following description of the preferred embodiments thereof, and from the claims.

DESCRIPTION OF THE PREFERRED EMBODIMENT

Figure 1:
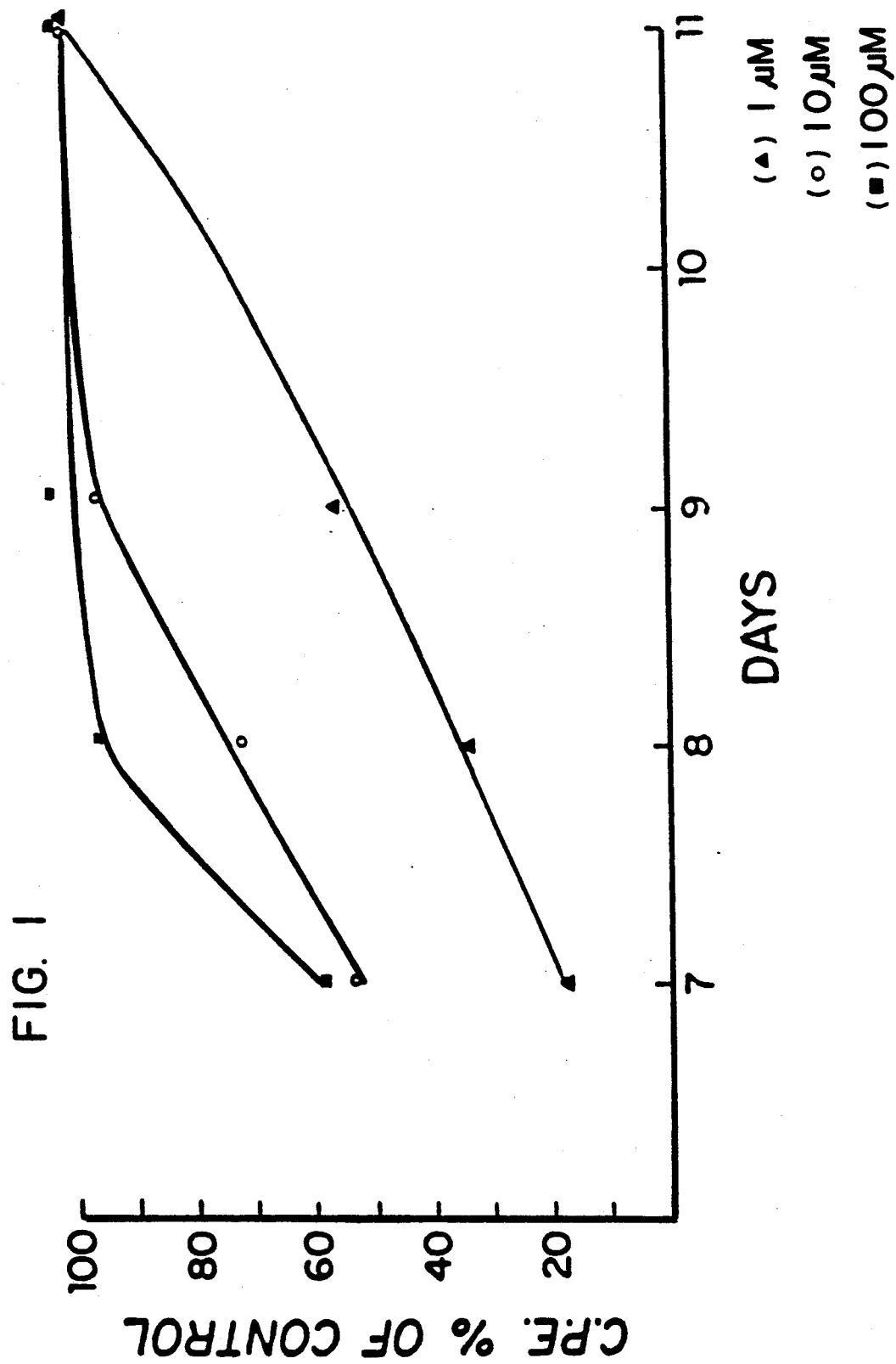
FIG. 1 is a graph showing the inhibition of HIV by antisense oligodeoxyribonucleoside methylphosphonates.

According to the present invention OMPs modeled as HIV antisense are synthesized. Since viral ribonucleic acid sequences are subject to much greater variation due to mutation, it is necessary to choose a viral sequence in which the variation is expected to be minimal. Focusing on functional sequences of a gene (splice sites, reverse transcriptase (RT) priming site) and comparing the available sequence information for sequences in common minimizes the variation problem.

SYNTHESIS OF OMPs MODELED AS HIV ANTISENSE

In this invention one of the trans-activator genes (tat III) of HIV was chosen as the gene on which an antisense OMP was modeled. The tat III gene has been shown to play a role in the regulation of expression of the other viral genes.[5] The tat protein positively regulates viral gene expression by an enhancement of the translation efficiency of virus-specific mRNA species. This effect of the tat protein requires that the TAR sequences mapping within the R region of the LTR be located at or near the 5' terminus of the mRNA. The tat gene has been shown to be essential for virus replication in T4+ CEO lines.

[5] Sodroski, J., et al., *Science* 227: 171-173 (1985); Arya, S. K., et al., *Science* 229: 69-73 (1985); Sodroski, J., et al., *Science* 229: 74-77 (1985)'.

According to the present invention an 8 base OMP complementary to the first splice acceptor site of this gene was designed and used as an anti-HIV agent. The 8 base OMP of the present invention attacks this splice acceptor site to block the splicing of the RNA product of the tat III gene and eventually inhibit viral replication. The splice site sequence is conserved in two different HIV isolates, and therefore if the antisense sequence is effective as an antiviral, it should be effective against a wide variety, if not all HIV strains. As a control, a second OMP was made which has the same sequence as the splice signal, and thus is termed a "sense OMP". The antisense OMP is referred to as OMP-A and the sense OMP is referred to as OMP-C.

Below is shown the portion of the RNA sequence of the first splice acceptor site of the tat III gene (5'... AGAAUUGG... 3').

```
                        splice acceptor site
                                |
5850 CCAUUUUCAGAAUUGGGUGUCGACAUAGCAGAAUAGGCGUUACUCGACAG 5850
(5')                                                    (3')

OMP-A  3'TCTTAACC 5' antisense
OMP-C  5'AGAATTGG 3' sense
```

The OMPs used in accordance with the present invention were synthesized from methylphosphonamidites using a solid phase reaction and were purified by ion exchange chromatography as is known in the art.

In general, short OMPs (8-15 bases in length) complementary to different regions of the HIV genome can be synthesized and tested to determine which other target sites in HIV are critical for expression of viral genes and viral replication and therefore susceptible to attack by antisense inhibition sequences.

Other target sites that will be attacked by antisense oligodeoxynucleotides and oligodeoxynucleoside agents can be determined based upon the published sequences and biological studies of HIV. Examples of other target sites are the splice donor sites centered near nucleotides 287 and 5625, and the splice acceptor sites centered near nucleotide 5358 and nucleotide 7956, all of which can be used as models for antisense oligos to inhibit tat III splicing. See, Arya, S. K., et al., *Science* 229: 69-73 (1985). As a further example, Sodroski, J., et al., *Nature* 321: 412-417 (1986) discuss the ART gene (anti-repression trans-activator) product as another important regulatory product necessary for protein mRNAs. Antisense oligos complementary to the splice donor site in the vicinity of position 5625 and the splice acceptor site centered at nucleotide 7956 also can be made in accordance with the present invention.

Oligos complementary to the tRNA priming site and regions 5' of this site have some inhibitory activity according to Zamecnik, P., et al., *PNAS USA* 83: 4143-4146 (1986). In order for complementary OMPs to be effective inhibitors, it is necessary to modify the 3' nucleotide of oligodeoxyribonucleotides so that it cannot serve as a primer by treatment with RNA ligase and pcp to generate a 3' phosphate terminus, or by using a dideoxy nucleoside at the 3' position in the oligo synthesis. The sequence of this oligo is complementary to the sequence centered at position 190 in the viral RNA sequence, which is the site of the tRNA priming activity.

INHIBITION OF PRIMARY HIV INFECTION WITH OMPs

H9 human lymphoid cells were polybrene-treated, incubated with varying concentrations of OMP for one hour, washed, and then infected with HIV (strain HTLV-III$_B$, 0.01 reverse transcriptase (RT) units per $10^6$ cells). The antiviral observations were based on induction of syncytial giant cell formation (cytopathogenic effect (CPE)) and RT activity. Syncytial giant cell formation was apparent within 3-4 days and peaked on day 7 post infection. Quantitation of viral CPE was made by enumeration of giant infected cells. These methods are further described in copending application Ser. No. 032,272 filed Jun. 3, 1987.

The development of multinucleated cells (CPE), RT activity, p24 (an HIV antigen), and viral RNA was inhibited by a single exposure to OMP-A, but not OMP-C. In chronically HIV-infected cells, OMP-A treatment inhibited RT activity. Neither of the OMPs induced any cellular toxicity in uninfected H9 cells.

As shown in FIG. 1, CPE was inhibited by OMP-A, the antisense construct, even at concentrations as low as 1 $\mu$M, but the most dramatic reduction in giant cell formation required 100 $\mu$M OMP-A. By days 8-11 after treatment, the inhibitory effect of the drug was lost. As shown in Table I below, the control OMP-C produced no inhibition of CPE. Treatment of the cells with OMP-C only minimally (<10%) inhibited RT. Because the H9 cells were exposed to the OMP for only one hour, it is not unexpected that the antiviral effect was transient.

TABLE I

| | Potency Testing of OMPs | |
|---|---|---|
| Days Post Treatment | OMP-A[a/] | OMP-C[b/] |
| 7 | 10[c/] | >>100 |
| 8 | 40 | >>100 |
| 9 | 100 | >>100 |
| 11 | >>100 | >>100 |

[a/] OMP-A = 5' CCAATTCT 3' targeted to first tat III splice site.
[b/] OMP-C = 3'GGTTAAGA 5' is the control "sense" sequence for this site.
[c/] Antiviral potency is expressed as the OMP concentration at which 50% inhibition of syncytial giant cell formation was observed. Data is derived from three experiments.

A modified polymerase chain reaction amplification assay was also used in accordance with the present invention to determine the effect of the OMP treatment on viral RNA synthesis. Details of this amplification procedure are disclosed in copending application Ser. No. 941,379, filed Dec. 15, 1986 with the exception that a modified version of the HIV 3'ORF region is constructed such that the sequences between the two primer sites are altered in length and composition. Such a modification allows for a control RNA or DNA template of fixed concentration to be made which is included with the experimental RNA or DNA samples. The probe for identifying this altered sequence is different from that used for the HIV samples, thereby enabling differentiation of the template amplification from the HIV sequence amplification. The amount of the altered template remains constant thereby enabling one to determine the ratio of amplification of the altered template versus the authentic HIV templates.

Briefly, to perform the amplification assay, two converging oligonucleotide primers, oriented in opposite directions, were added to RNA isolated from infected H9 cells on day 6 after HIV infection. Using RT, DNA amplification of the bracketed RNA site was performed with 6 cycles of transcription and then, using DNA polymerase I, was amplified in 14 additional cycles of transcription. Detection of this amplified DNA was performed by Southern blot analysis using as a probe a third synthetic oligonucleotide complementary to a region within the amplified segment. Using this technique, as few as 100 molecules of RNA can be detected.

Figure 2:
FIG. 2 is a photographic exposure showing the results of amplification and detection with probes of HIV RNAs treated with oligodeoxyribonucleoside methylphosphonates.

OMP-A greatly reduced the amount of RNA detectible in infected cells as seen in the assay results of FIG. 2. To obtain the results in FIG. 2, the OMP-A and OMP-C OMPs were added to cells as described above. RNA was derived from cells incubated 6 days post treatment. The lanes shown in FIG. 2 are as follows: A, in vitro transcript of amplified region with $10^{-7}$ pmoles of input RNA; B, control sample from HIV infected cells treated with a 100 μM concentration of a non-specific OMP complementary to HSV I (herpes simplex virus I) sequences; C and D, positive controls from cells infected with HIV in the absence of OMP treatment; E, sample from HIV infected cells pretreated with OMP-C, the sense sequence; F, sample from HIV infected cells pretreated with OMP-A, the antisense sequence. For each reaction involving HIV infected cells, 1 ugm of total cellular RNA was used for the amplification. After the amplified DNA were subjected to gel electrophoresis, blotted to a nylon filter membrane, and hybridized to detection probes, the filter was exposed to x-ray film for 12 hours to obtain the exposure of FIG. 2.

CENTRAL NERVOUS SYSTEM AXONAL TRANSPORT OF ANTI-VIRAL OLIGONUCLEOTIDES

It is known that subacute encephalitis from HIV infection of the central nervous system (CNS) is common in AIDS, occurring in about one-third of autopsied cases. Another aspect of the present invention is the use of antisense oligonucleotides to the tat III gene as described above to inhibit HIV replication in established CNS cell lines which have been shown to be permissive for HIV replication. Such CNS cell lines are reported by Cheng-Mayer, et al., *PNAS USA* 84: 3526 (1987).

The axonal transport or other delivery of antisense oligonucleotides such as the 8 base OMP described above is increased by modifications of the oligonucleotides designed to increase the uptake and transport such as addition of a polylysine residue covalently conjugated at the 3' end of the oligodeoxynucleotides and coupling oligodeoxynucleotides to a carrier protein that is efficiently transported.

We claim:

1. An oligodeoxyribonucleoside methylphosphonate with the sequence 3' TCTTAACC 5'.

2. A purified synthetic oligodeoxynucleotide methylphosphonate consisting essentially of the sequence 3' TCTTAACC 5'.

3. A purified synthetic oligodeoxynucleotide methylphosphonate as defined by claim 2 which is 8-15 bases in length.

4. A method for inhibiting in vitro the formation of syncytial giant cells in HIV infected H-9 human lymphoid cells which comprises exposing said infected cells to an oligodeoxyribonucleoside methylphosphonate sequence complementary to the first splice acceptor site of the TAT III gene of the HIV with which said H-9 human lymphoid cells are infected.

5. A method as defined by claim 4 in which the HIV with which said H-9 human lymphoid cells are infected is strain HTLV-IIIB.

* * * * *